(12) United States Patent
Matsuzaki et al.

(10) Patent No.: US 11,787,753 B2
(45) Date of Patent: Oct. 17, 2023

(54) METHANE PRODUCTION APPARATUS, METHANE PRODUCTION METHOD, CARBON DIOXIDE RECOVERY APPARATUS, AND CARBON DIOXIDE RECOVERY METHOD

(71) Applicants: TOKYO GAS CO., LTD., Tokyo (JP); THE UNIVERSITY OF TOKYO, Tokyo (JP)

(72) Inventors: Yoshio Matsuzaki, Tokyo (JP); Yoshitaka Baba, Tokyo (JP); Koki Sato, Tokyo (JP); Hiroki Iinuma, Tokyo (JP); Junichiro Otomo, Tokyo (JP)

(73) Assignees: TOKYO GAS CO., LTD., Tokyo (JP); THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 17/624,733

(22) PCT Filed: Jul. 14, 2020

(86) PCT No.: PCT/JP2020/027358
§ 371 (c)(1),
(2) Date: Jan. 4, 2022

(87) PCT Pub. No.: WO2021/015056
PCT Pub. Date: Jan. 28, 2021

(65) Prior Publication Data
US 2022/0204422 A1 Jun. 30, 2022

(30) Foreign Application Priority Data
Jul. 19, 2019 (JP) ................. 2019-133519

(51) Int. Cl.
*C07C 1/12* (2006.01)
*B01J 20/04* (2006.01)
*B01J 23/755* (2006.01)
*B01D 53/62* (2006.01)
*B01D 53/81* (2006.01)

(52) U.S. Cl.
CPC ................ *C07C 1/12* (2013.01); *B01D 53/62* (2013.01); *B01D 53/81* (2013.01); *B01J 20/043* (2013.01); *B01J 23/755* (2013.01); *B01D 2251/306* (2013.01); *B01D 2251/604* (2013.01); *B01D 2251/606* (2013.01); *B01D 2257/504* (2013.01); *B01D 2257/80* (2013.01); *B01J 2220/42* (2013.01); *C07C 2523/755* (2013.01)

(58) Field of Classification Search
CPC ........ B01D 53/62; B01D 53/81; B01J 20/043; B01J 23/755
See application file for complete search history.

(56) References Cited

U.S. PATENT DOCUMENTS

2008/0072760 A1 3/2008 Imada et al.

FOREIGN PATENT DOCUMENTS

| EP | 3501632 A1 | 6/2019 |
|---|---|---|
| JP | 2008-105006 A | 5/2008 |
| JP | 2013-136538 A | 7/2013 |
| JP | 2014-231504 A | 12/2014 |
| JP | 2014231504 A * | 12/2014 |
| JP | 2019-108290 A | 7/2019 |

OTHER PUBLICATIONS

Fasihi et al., Journal of Cleaner Production, (2019), v.224, p. 957-980. (Disclosed in IDS).*
Guo et al., Energy & Fuels, (2018), v32, p. 3681-3689.*
Jun. 23, 2020, Japanese Office Action issued for related JP Application No. 2019-133519.
Nov. 17, 2020, Japanese Office Action issued for related JP Application No. 2019-133519.
Sep. 8, 2020, International Search Report issued for related PCT application No. PCT/JP2020/027358.
Fasihi et al., Techno-economic assessment of $CO_2$ direct air capture plants, Journal of Cleaner Production, Mar. 14, 2019, pp. 957-980, Elsevier.
Jan. 13, 2023, Indonesian Office Action issued for related ID Application No. P00202201014.

* cited by examiner

*Primary Examiner* — Yong L Chu
(74) *Attorney, Agent, or Firm* — Paratus Law Group, PLLC (57) ABSTRACT

A methane production apparatus (200) includes: a holding unit (110) configured to hold any one or both of: a metal organic framework containing any one or a plurality of chromium, copper, and magnesium, and storing carbon dioxide; and potassium bicarbonate; and a hydrogen supply unit (140) configured to supply hydrogen to the holding unit (110).

3 Claims, 5 Drawing Sheets

METHANE PRODUCTION APPARATUS, METHANE PRODUCTION METHOD, CARBON DIOXIDE RECOVERY APPARATUS, AND CARBON DIOXIDE RECOVERY METHOD

CROSS REFERENCE TO RELATED APPLICATIONS

This application is a continuation application of International Application No. PCT/JP2020/027358, filed on Jul. 14, 2020, which claims priority to Japanese Patent Application No. 2019-133519 filed on Jul. 19, 2019, the entire contents of which are incorporated by reference herein.

BACKGROUND ART

The present invention relates to a methane production apparatus, a methane production method, a carbon dioxide recovery apparatus, and a carbon dioxide recovery method.

RELATED ART

In recent years, there has been developed a technology for producing methane by allowing carbon dioxide and hydrogen to react with each other. For example, in Patent Literature 1, there is a description of a methanation reaction apparatus including: a first reactor accommodating a catalyst; a raw material gas supply line for supplying a raw material gas rich in carbon dioxide to the first reactor; and a hydrogen supply line for supplying hydrogen to the first reactor.

CITATION LIST

Patent Literature

Patent Literature 1: JP 2013-136538 A

SUMMARY

Technical Problem

The above-mentioned methanation reaction for converting carbon dioxide and hydrogen into methane is an exothermic reaction. Accordingly, a local increase in temperature occurs in the reactor in some cases. In those cases, there is a risk in that the catalyst accommodated in the reactor may be deteriorated, or the reactor itself may be broken.

In view of such problem, an object of the present invention is to provide a methane production apparatus, a methane production method, a carbon dioxide recovery apparatus, and a carbon dioxide recovery method that are capable of producing methane while suppressing a temperature increase.

Solution to Problem

In order to solve the above-mentioned problem, according to one embodiment of the present invention, there is provided a methane production apparatus, including: a holding unit configured to hold any one or both of: a metal organic framework containing any one or a plurality of chromium, copper, and magnesium, and storing carbon dioxide; and potassium bicarbonate; and a hydrogen supply unit configured to supply hydrogen to the holding unit.

In order to solve the above-mentioned problem, according to one embodiment of the present invention, there is provided a methane production method, including a step of supplying hydrogen to any one or both of: a metal organic framework containing any one or a plurality of chromium, copper, and magnesium, and storing carbon dioxide; and potassium bicarbonate.

In order to solve the above-mentioned problem, according to one embodiment of the present invention, there is provided a carbon dioxide recovery apparatus, including: a holding unit configured to hold one or a plurality selected from the group consisting of: a metal organic framework containing any one or a plurality of chromium, copper, and magnesium; potassium carbonate; and potassium hydroxide; a gas-to-be-treated supply unit configured to supply a gas to be treated, which at least contains carbon dioxide and water, to the holding unit; and a hydrogen supply unit configured to supply hydrogen to the holding unit.

In order to solve the above-mentioned problem, according to one embodiment of the present invention, there is provided a carbon dioxide recovery method, including the steps of: supplying a gas to be treated, which at least contains carbon dioxide and water, to one or a plurality selected from the group consisting of: a metal organic framework containing any one or a plurality of chromium, copper, and magnesium; potassium carbonate; and potassium hydroxide; and supplying hydrogen to any one or both of: a metal organic framework storing carbon dioxide; and potassium bicarbonate, which are generated by the supplying a gas to be treated.

Effects of Disclosure

According to the present invention, methane can be produced while a temperature increase is suppressed.

DESCRIPTION OF EMBODIMENTS

Now, with reference to the attached drawings, preferred embodiments of the present invention are described in detail. The dimensions, materials, and other specific numerical values represented in the embodiments are merely examples used for facilitating the understanding of the invention, and do not limit the present invention otherwise particularly noted. Elements having substantially the same functions and configurations herein and in the drawings are denoted by the same reference symbols to omit redundant description thereof. In addition, illustration of elements with no direct relationship to the present invention is omitted.

Carbon dioxide ($CO_2$) is a factor of global warming. Accordingly, the amount of emission of carbon dioxide to the atmosphere is regulated by the United Nations Framework Convention on Climate Change and the like. In view of this, there has been developed a technology for directly removing carbon dioxide from a gas containing carbon dioxide (e.g., air) ($CO_2$ direct air capture (DAC)) (for example, Non-Patent Literature 1: Mahdi Fasihi et al., Journal of Cleaner Production 224 (2019) 957-980).

In Non-Patent Literature 1, first, air and an absorbent material (e.g., potassium carbonate) are brought into contact with each other to allow carbon dioxide in the air and potassium carbonate to react with each other to produce potassium bicarbonate. Thus, carbon dioxide is removed from the air. Meanwhile, potassium bicarbonate is heated to about 200° C. to be thermally decomposed into potassium carbonate and carbon dioxide. Thus, high-concentration carbon dioxide is recovered, and at the same time, potassium bicarbonate is regenerated into potassium carbonate.

In the related-art DAC described in Non-Patent Literature 1 above, an endothermic reaction at about 200° C. needs to be performed in order to regenerate the absorbent material, and hence there is a problem in that high energy is required.

In view of the foregoing, in an embodiment of the present invention, a carbon dioxide recovery apparatus capable of recovering carbon dioxide with lower energy as compared to the related-art DAC is described.

[Carbon Dioxide Recovery Apparatus 100]

Figure 1:
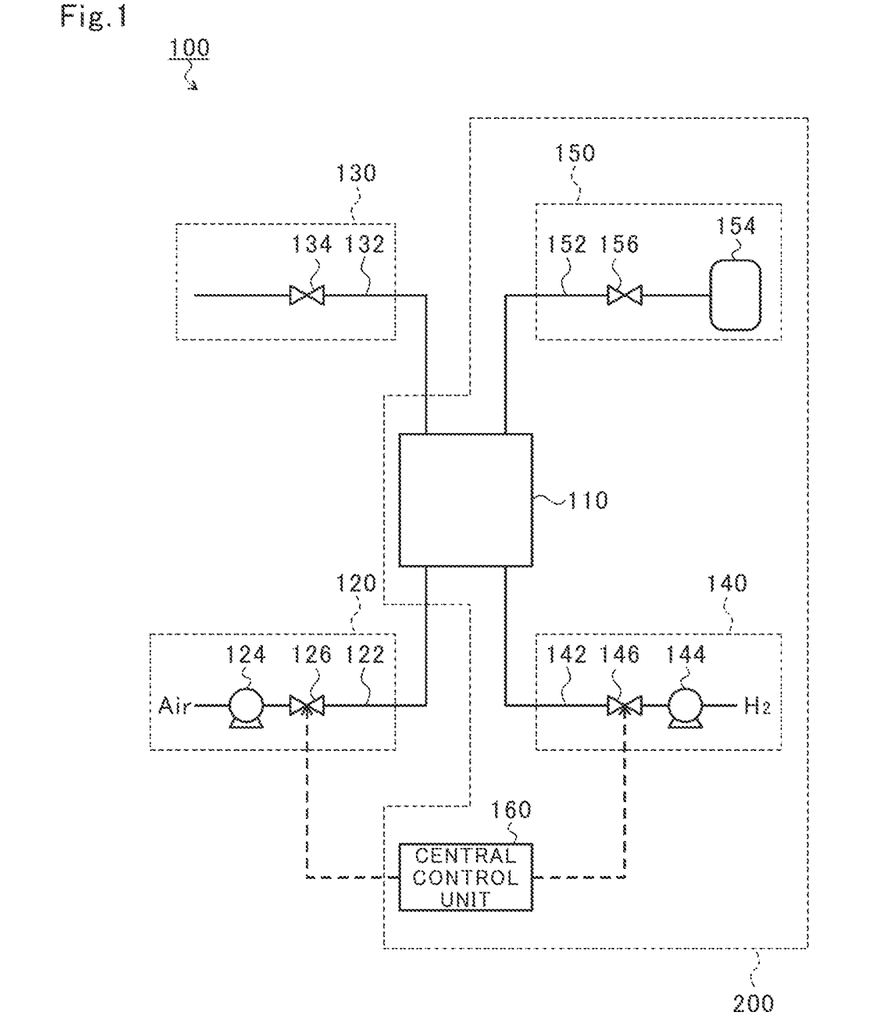
FIG. 1 is an explanatory diagram of a carbon dioxide recovery apparatus according to an embodiment of the present invention.

FIG. 1 is an explanatory diagram of a carbon dioxide recovery apparatus 100 according to this embodiment. As illustrated in FIG. 1, the carbon dioxide recovery apparatus 100 includes a holding unit 110, a gas-to-be-treated supply unit 120, a first exhaust unit 130, a hydrogen supply unit 140, a second exhaust unit 150, and a central control unit 160. In FIG. 1, dashed arrows indicate the flow of signals. For the purpose of simplifying the illustration, in FIG. 1, dashed lines representing the flow of signals from the central control unit 160 to on-off valves 134 and 156 are not shown.

The holding unit 110 holds an absorbent material and a catalyst. In this embodiment, the holding unit 110 includes: a main body having a honeycomb structure; an absorbent material and a catalyst that are supported by the main body; and a temperature retaining portion for retaining the temperature of the main body at a predetermined temperature (e.g., 200° C.). The absorbent material contains any one or both of potassium carbonate ($K_2CO_3$) and potassium hydroxide (KOH). The catalyst is a catalyst for promoting a methanation reaction between carbon dioxide and hydrogen ($H_2$). The catalyst is, for example, a nickel (Ni)-based catalyst.

The gas-to-be-treated supply unit 120 supplies a gas to be treated to the holding unit 110. The gas to be treated at least contains carbon dioxide and water ($H_2O$, water vapor). Herein, a case in which the gas to be treated is air is taken as an example. In this embodiment, the gas-to-be-treated supply unit 120 includes a gas-to-be-treated supply pipe 122, a blower 124, and an on-off valve 126. One end of the gas-to-be-treated supply pipe 122 is open to the atmosphere, and the other end thereof is connected to one end side of the holding unit 110. The blower 124 is arranged in the gas-to-be-treated supply pipe 122. The suction side of the blower 124 is connected to the open end, and the discharge side thereof is connected to the holding unit 110. The on-off valve 126 is arranged in the middle of the gas-to-be-treated supply pipe 122 between the blower 124 and the holding unit 110. The on-off valve 126 opens and closes a flow passage formed in the gas-to-be-treated supply pipe 122.

The first exhaust unit 130 discharges a first exhaust gas from the holding unit 110. The first exhaust gas is a gas obtained by removing carbon dioxide from air (gas to be treated). In this embodiment, the first exhaust unit 130 includes a first exhaust pipe 132 and the on-off valve 134. One end of the first exhaust pipe 132 is open to the atmosphere, and the other end thereof is connected to the other end side of the holding unit 110. The on-off valve 134 is arranged in the first exhaust pipe 132. The on-off valve 134 opens and closes a flow passage formed in the first exhaust pipe 132.

The hydrogen supply unit 140 supplies hydrogen to the holding unit 110. In this embodiment, the hydrogen supply unit 140 includes a hydrogen supply pipe 142, a blower 144, and an on-off valve 146. The hydrogen supply pipe 142 connects a hydrogen supply source to the one end side of the holding unit 110. The blower 144 is arranged in the hydrogen supply pipe 142. The suction side of the blower 144 is connected to the hydrogen supply source, and the discharge side thereof is connected to the holding unit 110. The on-off valve 146 is arranged in the middle of the hydrogen supply pipe 142 between the blower 144 and the holding unit 110. The on-off valve 146 opens and closes a flow passage formed in the hydrogen supply pipe 142.

The second exhaust unit 150 discharges a second exhaust gas from the holding unit 110. The second exhaust gas contains methane ($CH_4$) and water (water vapor). In this embodiment, the second exhaust unit 150 includes a second exhaust pipe 152, a methane storage portion 154, and the on-off valve 156. The second exhaust pipe 152 connects the other end side of the holding unit 110 to the methane storage portion 154. The methane storage portion 154 stores the second exhaust gas. The on-off valve 156 is arranged in the middle of the second exhaust pipe 152 between the holding unit 110 and the methane storage portion 154. The on-off valve 156 opens and closes a flow passage formed in the second exhaust pipe 152.

The central control unit 160 includes a semiconductor integrated circuit including a central processing unit (CPU). The central control unit 160 reads out, for example, a program or parameters for operating the CPU itself from a ROM. The central control unit 160 manages and controls the entire carbon dioxide recovery apparatus 100 in cooperation with a RAM serving as a working area and other electronic circuits. In this embodiment, the central control unit 160 controls the opening and closing of the on-off valves 126, 134, 146, and 156, and controls the drive of the blowers 124 and 144.

[Carbon Dioxide Recovery Method]

Figure 2:
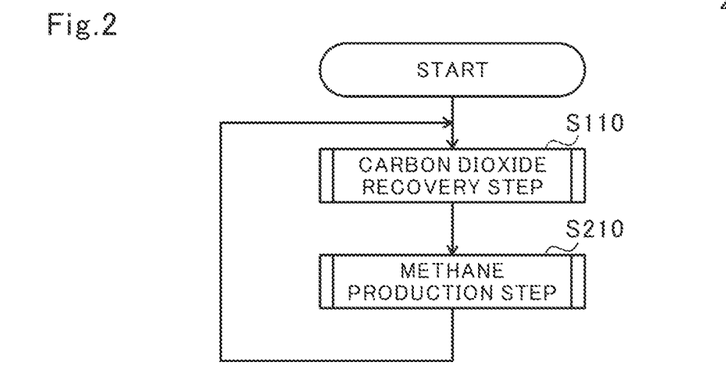
FIG. 2 is a flowchart for illustrating the flow of treatment in a carbon dioxide recovery method according to an embodiment of the present invention.

Next, a carbon dioxide recovery method using the carbon dioxide recovery apparatus 100 is described. FIG. 2 is a flowchart for illustrating the flow of treatment in the carbon dioxide recovery method according to this embodiment. As illustrated in FIG. 2, the carbon dioxide recovery method includes a carbon dioxide recovery step S110 and a methane production step S210. In the carbon dioxide recovery method, the carbon dioxide recovery step S110 and the methane production step S210 are alternately carried out. In addition, in this embodiment, the carbon dioxide recovery method is repeatedly carried out by virtue of interrupts that occur at predetermined time intervals. The carbon dioxide recovery step S110 and the methane production step S210 are described in detail below.

[Carbon Dioxide Recovery Step S110]

Figure 3:
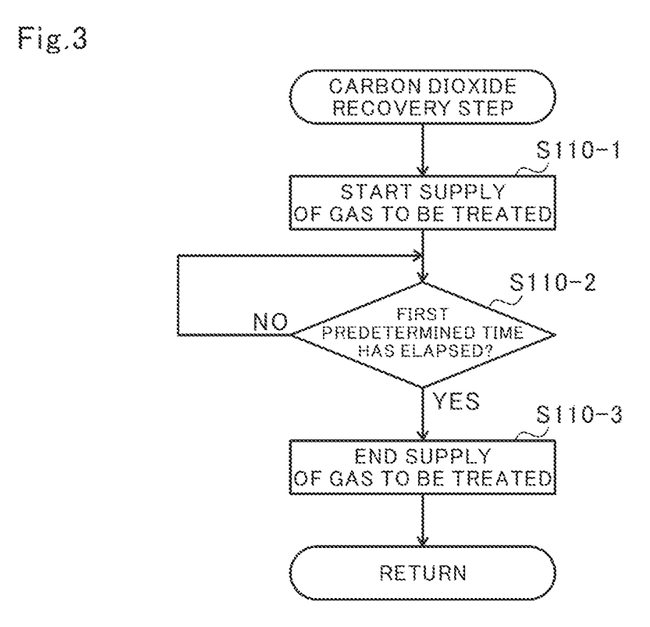
FIG. 3 is a flowchart for illustrating the flow of treatment in a carbon dioxide recovery step.
Figure 4:
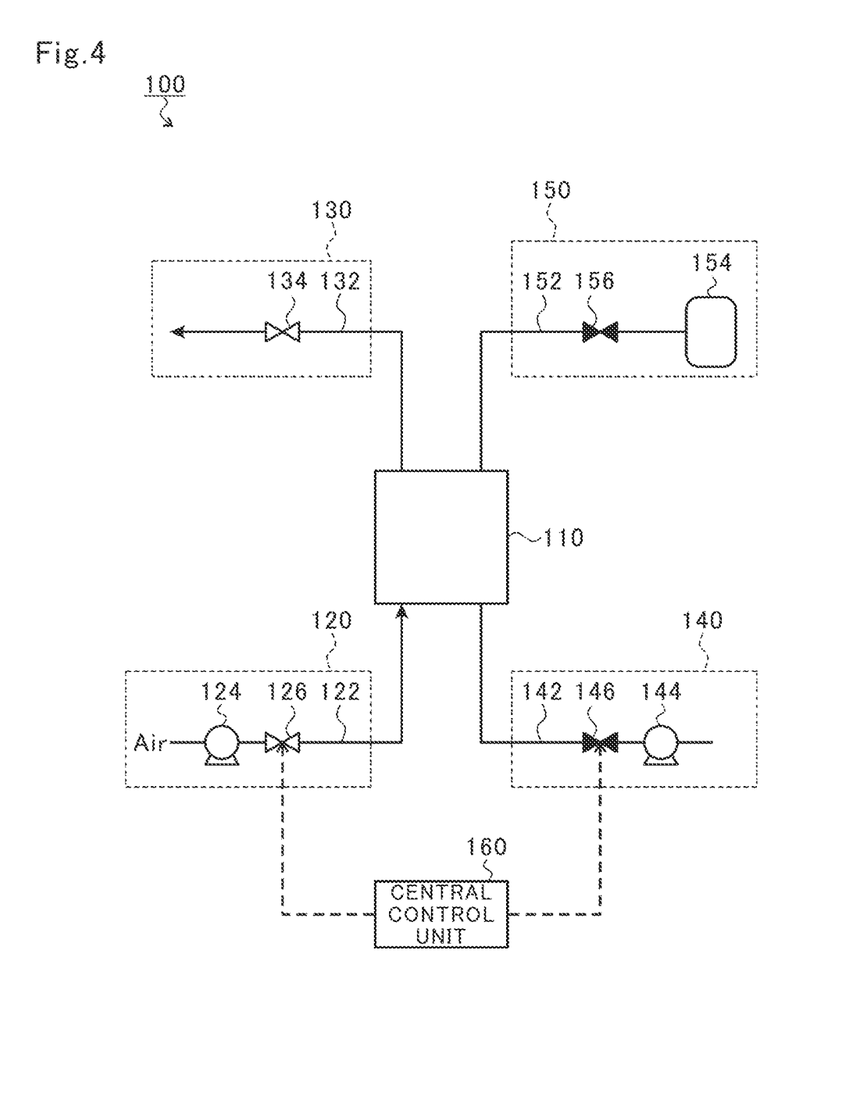
FIG. 4 is an explanatory diagram of the control of on-off valves and blowers by a central control unit in the carbon dioxide recovery step.

FIG. 3 is a flowchart for illustrating the flow of treatment in the carbon dioxide recovery step S110. FIG. 4 is an explanatory diagram of the control of the on-off valves 126, 134, 146, and 156, and the blowers 124 and 144 by the central control unit 160 in the carbon dioxide recovery step S110. In FIG. 4, the closed states of the on-off valves 146 and 156 are represented by black fill. In addition, in FIG. 4, solid arrows indicate the flow of gases.

As illustrated in FIG. 3, the carbon dioxide recovery step S110 includes a gas-to-be-treated supply starting step S110-1, a first predetermined time lapse determination step S110-2, and a gas-to-be-treated supply ending step S110-3.

[Gas-to-be-Treated Supply Starting Step S110-1]

The central control unit 160 opens the on-off valves 126 and 134, and drives the blower 124. Thus, air is led into the holding unit 110 through the gas-to-be-treated supply pipe 122. Consequently, a reaction shown in the following formula (1) proceeds. When the holding unit 110 holds potassium hydroxide, the reaction shown in the following formula (1) proceeds as well as a reaction shown in the following formula (2).

$$K_2CO_3 + CO_2 + H_2O \rightarrow 2KHCO_3 \quad \text{Formula (1)}$$

$$2KOH + CO_2 + H_2O \rightarrow K_2CO_3 + 2H_2O \quad \text{Formula (2)}$$

Accordingly, when the gas-to-be-treated supply starting step S110-1 is carried out, the absorbent material (potassium carbonate) held in the holding unit 110 removes carbon dioxide from the air. The air from which carbon dioxide has been thus removed is discharged to the outside through the first exhaust pipe 132.

[First Predetermined Time Lapse Determination Step S110-2]

The central control unit 160 determines whether or not a first predetermined time has elapsed. When it is determined as the result that the first predetermined time has elapsed (YES in Step S110-2), the central control unit 160 proceeds with the treatment to the gas-to-be-treated supply ending step S110-3. Meanwhile, when it is determined that the first predetermined time has not elapsed (NO in Step S110-2), the central control unit 160 repeats the first predetermined time lapse determination step S110-2. The first predetermined time is determined on the basis of a period of time from the start of the gas-to-be-treated supply starting step S110-1 until the absorbent material can no longer fully absorb carbon dioxide.

[Gas-to-be-Treated Supply Ending Step S110-3]

The central control unit 160 stops the blower 124, and closes the on-off valves 126 and 134.

[Methane Production Step S210 (Methane Production Method)]

Figure 5:
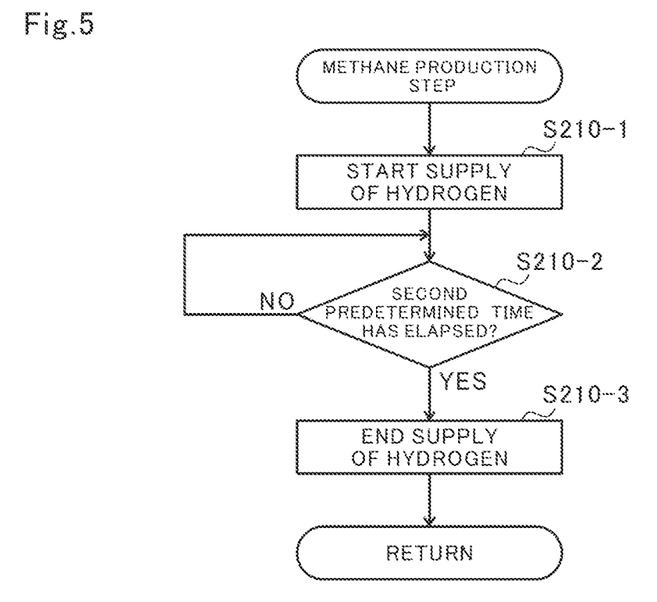
FIG. 5 is a flowchart for illustrating the flow of treatment in a methane production step.
Figure 6:
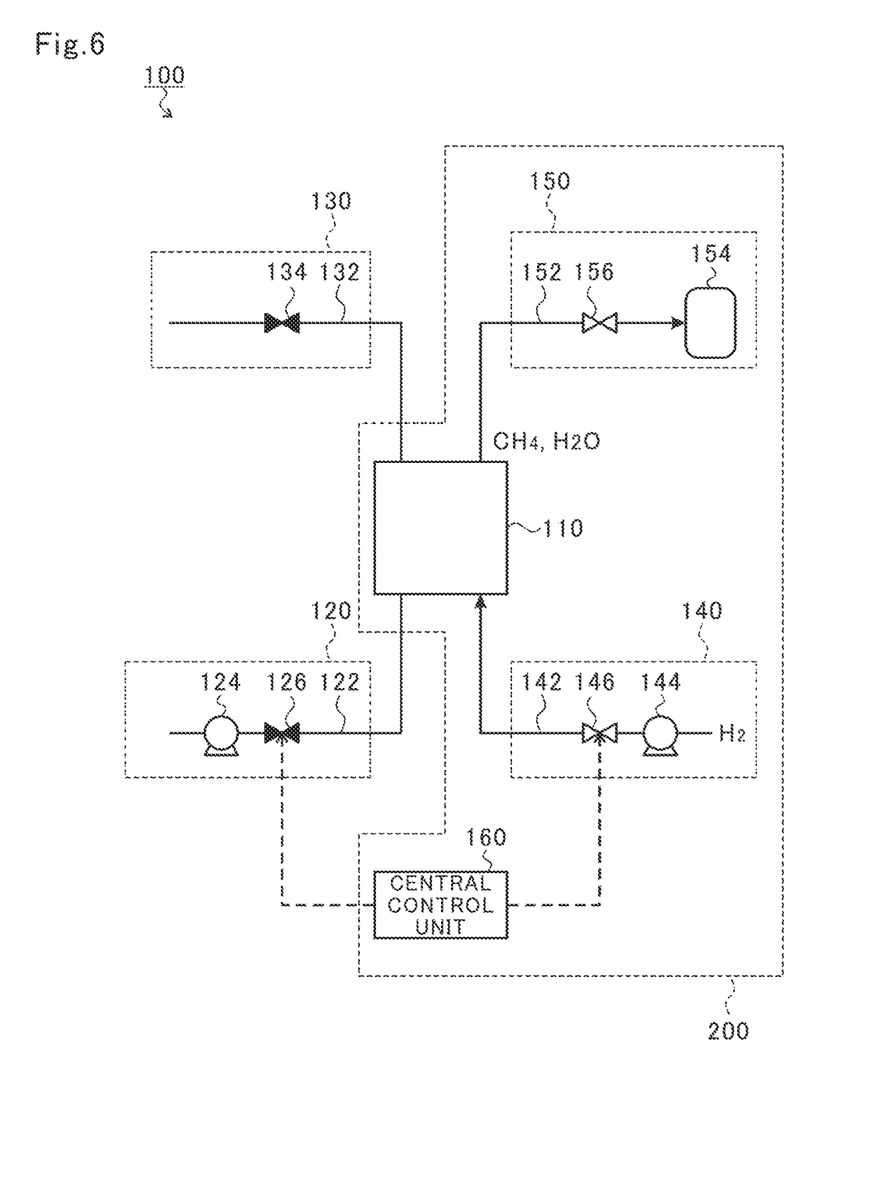
FIG. 6 is an explanatory diagram of the control of the on-off valves and the blowers by the central control unit in the methane production step.

FIG. 5 is a flowchart for illustrating the flow of treatment in the methane production step S210. FIG. 6 is an explanatory diagram of the control of the on-off valves 126, 134, 146, and 156, and the blowers 124 and 144 by the central control unit 160 in the methane production step S210. In FIG. 6, the closed states of the on-off valves 126 and 134 are represented by black fill. In addition, in FIG. 6, solid arrows indicate the flow of gases.

As illustrated in FIG. 5, the methane production step S210 includes a hydrogen supply starting step S210-1, a second predetermined time lapse determination step S210-2, and a hydrogen supply ending step S210-3.

[Hydrogen Supply Starting Step S210-1]

The central control unit 160 opens the on-off valves 146 and 156, and drives the blower 144. Thus, hydrogen is led into the holding unit 110 through the hydrogen supply pipe 142. Consequently, a reaction shown in the following formula (3) proceeds.

$$2KHCO_3 + 4H_2 \rightarrow K_2CO_3 + CH_4 + 3H_2O \quad \text{Formula (3)}$$

That is, when the hydrogen supply starting step S210-1 is carried out, the catalyst held in the holding unit 110 causes the reaction of the formula (3) to proceed to generate methane and water (water vapor) from the absorbent material having absorbed carbon dioxide (potassium bicarbonate). In addition, when the reaction of the formula (3) proceeds, the absorbent material having absorbed carbon dioxide is regenerated into the absorbent material (potassium carbonate). The thus generated methane and water vapor are led into the methane storage portion 154 through the second exhaust pipe 152.

[Second Predetermined Time Lapse Determination Step S210-2]

The central control unit 160 determines whether or not a second predetermined time has elapsed. When it is determined as the result that the second predetermined time has elapsed (YES in Step S210-2), the central control unit 160 proceeds with the treatment to the hydrogen supply ending step S210-3. Meanwhile, when it is determined that the second predetermined time has not elapsed (NO in Step S210-2), the central control unit 160 repeats the second predetermined time lapse determination step S210-2. The second predetermined time is determined on the basis of a period of time from the start of the hydrogen supply starting step S210-1 until methane is no longer generated from the absorbent material having absorbed carbon dioxide.

[Hydrogen Supply Ending Step S210-3]

The central control unit 160 stops the blower 144, and closes the on-off valves 146 and 156.

As described above, in the carbon dioxide recovery apparatus 100 and the carbon dioxide recovery method making use thereof according to the embodiments of the present invention, hydrogen is supplied to the holding unit 110 in the regeneration of the absorbent material having absorbed carbon dioxide (potassium bicarbonate). With this configuration, the reaction of the formula (3) can be carried out. Accordingly, the absorbent material can be regenerated (carbon dioxide can be recovered) with lower energy as compared to the related-art DAC.

Specifically, in the related-art DAC, potassium bicarbonate is regenerated into potassium carbonate by carrying out a thermal decomposition reaction shown in the following formula (A) through heating of potassium bicarbonate.

$$2KHCO_3 \rightarrow K_2CO_3 + CO_2 + H_2O \quad \text{Formula (A)}$$

The reaction enthalpy dH of the formula (A) is dH=+139.4 kJ (endothermic reaction).

Meanwhile, in the carbon dioxide recovery apparatus 100 according to this embodiment, potassium bicarbonate is regenerated into potassium carbonate by generating methane from the carbon atom (C) and oxygen atoms (2O) contained in potassium bicarbonate, and hydrogen ($H_2$) supplied by the hydrogen supply unit 140 (the formula (3)). That is, in the carbon dioxide recovery apparatus 100, a decomposition reaction of potassium bicarbonate into potassium carbonate, and a methane generation reaction are performed in parallel.

When methane is generated from carbon dioxide and hydrogen, a methanation reaction of the following formula (B) proceeds.

$$CO_2 + 4H_2 \rightarrow CH_4 \quad \text{Formula (B)}$$

The reaction enthalpy dH of the formula (B) is dH=−173.3 kJ (exothermic reaction).

Accordingly, in the carbon dioxide recovery apparatus 100, as the reaction of the formula (3) is carried out by supplying hydrogen to the holding unit 110 in the regeneration of the absorbent material having absorbed carbon dioxide (potassium bicarbonate), the energy required for the endothermic reaction of the formula (A) can be compensated for by the energy produced by the exothermic reaction of the formula (B).

Thus, the carbon dioxide recovery apparatus 100 can reduce the energy required for the regeneration of potassium bicarbonate to the reaction enthalpy dH=−34.0 kJ (exothermic reaction) of the formula (3).

That is, the carbon dioxide recovery apparatus 100 can regenerate the absorbent material with lower energy (reaction enthalpy dH=−34.0 kJ) as compared to the reaction enthalpy dH=+139.4 kJ of the related-art DAC.

In addition, the holding unit 110 holding the absorbent material having absorbed carbon dioxide (potassium bicarbonate), the hydrogen supply unit 140, and the second exhaust unit 150, which function as a methane production apparatus 200, carry out the reaction of the formula (3). Accordingly, as compared to the case of carrying out only the related-art methanation reaction of the formula (B), in the methane production apparatus 200, the energy produced by the exothermic reaction of the formula (B) can be absorbed by the energy required for the endothermic reaction of the formula (A). Thus, the methane production apparatus 200 can prevent a situation in which a local increase in temperature occurs in the holding unit 110 during the generation of methane. Accordingly, the methane production apparatus 200 can prevent a situation in which the catalyst accommodated in the holding unit 110 is deteriorated, or the holding unit 110 itself is broken.

In addition, the carbon dioxide recovery apparatus 100 can generate (produce) methane from carbon dioxide in air. Accordingly, the carbon dioxide recovery apparatus 100 can produce carbon neutral methane.

Preferred embodiments of the present invention have been described above with reference to the attached drawings, but, needless to say, the present invention is not limited to such embodiments. It is apparent that those skilled in the art could arrive at various alterations or modifications within the scope of the claims, and those alterations or modifications are construed as naturally falling within the technical scope of the present invention.

For example, in the above-mentioned embodiments, a configuration in which the holding unit 110 includes the main body having a honeycomb structure has been taken as an example. However, the configuration of the holding unit 110 is not limited as long as the holding unit 110 holds the absorbent material and the catalyst, and allows gases to pass therethrough. For example, the holding unit 110 may include: a main body having a cylindrical shape; a net portion arranged in a lower part of the main body; an absorbent material and a catalyst that are accommodated above the net portion; and a temperature retaining portion for retaining the temperature of the main body. In this case, a plurality of holes are formed in the net portion. In addition, the absorbent material and the catalyst are particles larger than the holes of the net portion.

In addition, in the above-mentioned embodiments, description has been made by taking air as an example of the gas to be treated. However, the gas to be treated only needs to at least contain carbon dioxide and water. The gas to be treated may be, for example, a combustion exhaust gas.

In addition, in the above-mentioned embodiments, potassium carbonate has been taken as an example of the absorbent material. However, the absorbent material is not limited to any substance as long as the substance absorbs carbon dioxide (reacts with carbon dioxide) and undergoes a carbon dioxide desorption reaction within a temperature range overlapping the temperature range of methanation. For example, the absorbent material may be a metal organic framework (MOF) containing any one or a plurality of chromium (Cr), copper (Cu), and magnesium (Mg). The metal organic framework (porous coordination polymer) is a substance formed of metal cations and a multidentate ligand bridging the cations.

When the MOF is adopted as the absorbent material, in the carbon dioxide recovery step 110, a reaction shown in the following formula (4) proceeds.

$$MOF+CO_2 \rightarrow MOF:CO_2 \quad \text{Formula (4)}$$

In the formula (4) and the following formula (5), MOF:$CO_2$ represents the MOF storing carbon dioxide.

In addition, in the methane production step S210, a reaction shown in the following formula (5) proceeds. The reaction shown in the formula (5) is an exothermic reaction like the reaction shown in the formula (3).

$$MOF:CO_2+4H_2 \rightarrow MOF+CH_4+2H_2O \quad \text{Formula (5)}$$

Meanwhile, the following formula (C), in which MOF:$CO_2$ is heated to desorb carbon dioxide, is an endothermic reaction like the reaction shown in the formula (A).

$$MOF:CO_2 \rightarrow MOF+CO_2 \quad \text{Formula (C)}$$

Accordingly, in the carbon dioxide recovery apparatus 100, also when the MOF containing any one or a plurality of chromium, copper, and magnesium is adopted as the absorbent material, the energy required for the endothermic reaction of the formula (C) can be compensated for by the energy produced by the exothermic reaction of the formula (B) because the reaction of the formula (5) is carried out by supplying hydrogen to the holding unit 110 in the regeneration of the absorbent material having absorbed carbon dioxide (MOF:$CO_2$).

In addition, in the methane production apparatus 200, also when the holding unit 110 holds the MOF containing any one or a plurality of chromium, copper, and magnesium, and storing carbon dioxide, the energy produced by the exothermic reaction of the formula (B) can be absorbed by the energy required for the endothermic reaction of the formula (C).

INDUSTRIAL APPLICABILITY

The present invention is applicable to a methane production apparatus, a methane production method, a carbon dioxide recovery apparatus, and a carbon dioxide recovery method.

REFERENCE SIGNS LIST

100: carbon dioxide recovery apparatus, 110: holding unit, 120: gas-to-be-treated supply unit, 140: hydrogen supply unit, 200: methane production apparatus

What is claimed is:
1. A methane production system comprising an apparatus and reactants contained therein which are undergoing a gas-solid reaction, wherein the apparatus comprises:
 a holding unit which has a main body, an absorbent material that is supported by the main body, and a catalyst that is supported by the main body; and
 a hydrogen supply unit configured to supply hydrogen to the holding unit to produce methane,
 wherein the absorbent material includes potassium bicarbonate, and the catalyst is a nickel-based catalyst, wherein the reaction takes place in the holding unit and is a gas-solid reaction, wherein the apparatus further comprises a gas-to-be-treated supply unit configured to supply a gas to be treated to the holding unit to absorb carbon dioxide contained in the gas to be treated into the absorbent material, wherein the apparatus is configured to supply the hydrogen to the holding unit at a different time than the gas to be treated is supplied to the holding unit, and wherein the methane production apparatus further comprises a central control unit that controls the hydrogen supply unit and the gas-to-be-treated supply unit, wherein the central control unit is configured to supply hydrogen to the holding unit at different times than the gas to be treated is supplied to the holding unit.

2. A carbon dioxide recovery method, comprising the steps of:

supplying a gas to be treated, which at least contains carbon dioxide and water, to the methane production system of claim 1.

3. The methane production system according to claim 1, wherein the central control unit is configured to deliver the hydrogen to the holding unit after the gas to be treated has been delivered to the holding unit.

* * * * *